US006453795B1

(12) United States Patent
Eicher et al.

(10) Patent No.: US 6,453,795 B1
(45) Date of Patent: Sep. 24, 2002

(54) LOCKING MECHANISM FOR A SPRING-ACTUATED DEVICE

(75) Inventors: Joachim Eicher, Dortmund; Michael Schyra, Wulfrath; Richard Forster, Fensterbach, all of (DE)

(73) Assignee: Boehringer Ingelheim International GmbH (DE)

(*) Notice: Subject to any disclaimer, the term of this patent is extended or adjusted under 35 U.S.C. 154(b) by 0 days.

(21) Appl. No.: 09/077,942
(22) PCT Filed: Dec. 5, 1996
(86) PCT No.: PCT/EP96/05607
§ 371 (c)(1),
(2), (4) Date: Nov. 10, 1998
(87) PCT Pub. No.: WO97/20590
PCT Pub. Date: Jun. 12, 1997

(30) Foreign Application Priority Data

Dec. 5, 1995 (DE) ........................................ 195 45 226

(51) Int. Cl.[7] ................................................ F15B 15/26

(52) U.S. Cl. ........................ 92/23; 92/136; 128/200.22; 222/340; 267/172; 604/135

(58) Field of Search ........................... 222/340, 3, 387; 92/23, 136; 267/172; 128/200.22; 604/135

(56) References Cited

U.S. PATENT DOCUMENTS 3,114,370 A * 12/1963 Kayler ....................... 604/137
3,612,051 A 10/1971 Arce
4,260,082 A 4/1981 Rooney et al.
4,623,332 A * 11/1986 Lindmayer et al. ......... 604/135
4,699,154 A * 10/1987 Lindgren .................... 128/754
4,787,891 A 11/1988 Levin et al.
4,944,308 A * 7/1990 Akerfeldt .................... 128/754
5,167,632 A * 12/1992 Eid et al. .................... 604/136
5,263,475 A 11/1993 Altermatt et al.
5,310,092 A 5/1994 Targell
5,388,572 A 2/1995 Mulhauser et al.
5,472,143 A 12/1995 Bartels et al.
5,497,944 A 3/1996 Weston et al.

FOREIGN PATENT DOCUMENTS

EP 0 318 447 5/1994
GB 2 291 135 1/1996
JP 56108877 8/1981
WO WO 92/20455 11/1992
WO WO 97/12687 4/1997

* cited by examiner

*Primary Examiner*—F. Daniel Lopez
(74) *Attorney, Agent, or Firm*—Sterne, Kessler, Goldstein & Fox P.L.L.C.

(57) ABSTRACT

A spring-actuated output drive device is used for example in medical aerosol therapy for a miniaturised high-pressure producing device for atomising a small dose of a liquid medicament. A locking-stressing-mechanism for such an output d rive device is to be stressed with the application of a relatively small amount of force and is to be released with one hand and is to operate reliably over a prolonged period of time. The locking-stressing-mechanism comprises a force step-up transmission, for example a screw thrust transmission for stressing the spring, an annularly arranged locking member with engaging locking surfaces, two abutments for limiting the travel of the spring and a release button. It is compact, economical to produce, easy to assemble and comprises components with a low rate of wear. It can be reliably and easily handled by unskilled persons, even when high spring forces are involved. A medicament to be atomised can thus be metered with a very high degree of accuracy.

7 Claims, 2 Drawing Sheets

LOCKING MECHANISM FOR A SPRING-ACTUATED DEVICE

The invention concerns a locking-stressing-mechanism for a spring-actuated output drive device and is particularly, though not exclusively, concerned with such a device by which a high pressure produced in a fluid for example by means of a piston in a cylinder.

One aim of the invention is to adapt such a locking-stressing-mechanism to the requirements of a miniaturized high-pressure producing device.

The invention has been particularly, though not exclusively, developed for application to metered dose inhalers (MDI's) such as are disclosed in U.S. Pat. No. 5,497,944 (derived from WO91/14468), the entire contents of both of which are incorporated herein by reference. Pressure (generally at least 50 bar) is generated in a metered amount of fluid which is discharged through a nozzle assembly having one or more very small openings e.g. in the range 25 to 500 square micrometers. Preferred nozzle assemblies are disclosed in U.S. Pat. No. 5,472,143 (and parallel WO94/07607), the entire contents of both of which are incorporated herein by reference. An energy storage means, such as a spring, is preferably manually loaded e.g. by a rotary sawtooth wedge arrangement as disclosed in U.S. Pat. No. 4,260,082 and GB Patent Application 2291135, the contents of both of which are incorporated herein by reference. A latching mechanism is generally provided to hold the spring in the loaded position and is manually releasable to pressurise the metered amount of fluid e.g. using a piston and cylinder arrangement. A reservoir and valve arrangement can be provide d for recharging the cylinder. Further details are described in PCT/EP96/04351 and parallel U.S. Pat. Ser. No. 08/726219, the entire contents of which are incorporated herein by reference.

In the known locking-stressing-mechanism (W. Krause: Konstruktionselemente der Feinmechanik, Verlag Carl Hanser, Munich 1993, pages 521 to 523) previously stored energy is liberated at the required moment and converted into movement. This means for storing the mechanical energy is generally a spring which is coupled to a guided or supported component, referred to as the quick-motion portion. A locking member presents the quick-motion position from moving and liberates it in a predetermined manner.

In medical aerosol therapy, aerosols produced by atomisation or spraying of liquid medicaments are used for treating ailments of the respiratory tracts in humans or for the treatment of asthmatic conditions. For that purpose, a high pressure in respect of the fluid is required in order to produce the small droplet size necessary for the aerosol The high pressure is generally produced by a piston movable in a cylinder (DE-OS 195 36 902.5). For a miniaturised hand-operated cylindrical atomiser of that kind, it is desirable or necessary to produce a relatively high mechanical force to drive the piston within the atomiser itself.

Accordingly another aim of the invention is to develop a locking-stressing-mechanism which, even in relation to high spring forces, is simple and reliable to operate.

In accordance with one aspect of the invention, there is provided a locking-stressing-mechanism for a spring actuated output drive device, which mechanism includes a spring as a storage means for the mechanical energy which acts on an output drive member as a quick-motion portion, the movement of which is determined by the position of a locking member, a drive for stressing the spring, an upper and a lower abutment for the output drive member and a means for releasing the locking member, the device having a force step-up transmission means between the drive for stressing the spring and the spring, and an annularly arranged locking member with engaging locking surfaces.

The energy storage means is preferably a coil spring or a plate or diaphragm spring which acts as a tension spring or as a compression spring and which is preferably cylindrical.

The spring can be stressed by means of a direct drive. For that purpose the output drive flange is displaced by an axially operative external force. In the case of a high spring force, it is advantageous to provide a force step-up transmission means, for example a screw thrust transmission means, by means of which the spring is stressed by an external torque which may tie manually applied. In the case of a screw thrust transmission means, an upper housing portion and the output drive member include a single-flight or multi-flight wedge drive. Such a transmission means is arranged between the drive for stressing the spring and the spring.

The locking member can be a ring which is radially elastically deformable in itself or a rigid ring with cam projections or a rigid ring with leaf springs formed thereon or a rigid ring which can be subjected to a spring prestressing effect by one or more metal springs. The ring can be closed or open and may comprise a plurality of and preferably two parts. The locking member comprises plastics material or metal. It is arranged displaceably in a plane perpendicularly to the cylinder axis or it is deformable in said plane.

After stressing of the spring the locking surfaces of the locking member move in 0o the path of the spring or the output drive member and prevent release of the spring.

The locking member is preferably actuated by means of a release button. The button may be coupled or connected to locking member. To release the locking-stressing-mechanism a release button of this kind and therewith the locking member are generally displaced parallel to the plane of the ring, more particularly and preferably towards the cylinder axis, or the locking member is radially deformed in the plane of the ring.

The travel of the output drive member is precisely delimited by defined abutments. Preferably the drive member is a flange on a further output member.

According to another aspect of the invention, there is provided a spring-loaded drive mechanism in which an output member is mounted for linear movement against the tension of a spring between a released position and a locked position and in which there is a locking member which can be moved transversely to the direction of movement of the output member into and out of the path of an abutment means associated with the output member, wherein the locking member is substantially in the form of an open or closed ring such that the abutment means can pass through it under the action of the spring when the mechanism is released and wherein the substantially ring-like locking member may optionally be in two or more sections.

Preferably the locking member forms an optionally interrupted closed ring but it could be in the form of an open ring or yoke. It is also desirable that the locking member engages the abutment means in such a way as to minimise the risk of tilting and binding of the output member. This may for example be achieved by arranging for engagement at least at two positions which are substantially diametrically opposite each other.

Other preferred features include the following:

The spring is a helical compression spring.

The locking member snaps into alignment with the abutment means when the output member reaches the locked position.

The snap action is provided by cams associated with means for moving the output member from the released position to the locked position.

The snap action is provided by one or more springs.

The locking member is resiliently deformable so as to provide the snap action.

The locking member is arranged to be manually moved out of the path of the abutment means.

There is a force step-up transmission for moving the output means against the bias of the spring.

The transmission comprises a rotatable part with a sawtooth thrust cam.

The output member is arranged to move a piston in a cylinder to compress fluid therein.

The mechanism is part of a device for spraying fluid or, more specifically, part of a metered dose atomiser.

Preferred embodiment of the invention will now be described, by way of example, with reference to the accompanying drawings, in which.

Figures 1A, 1B:
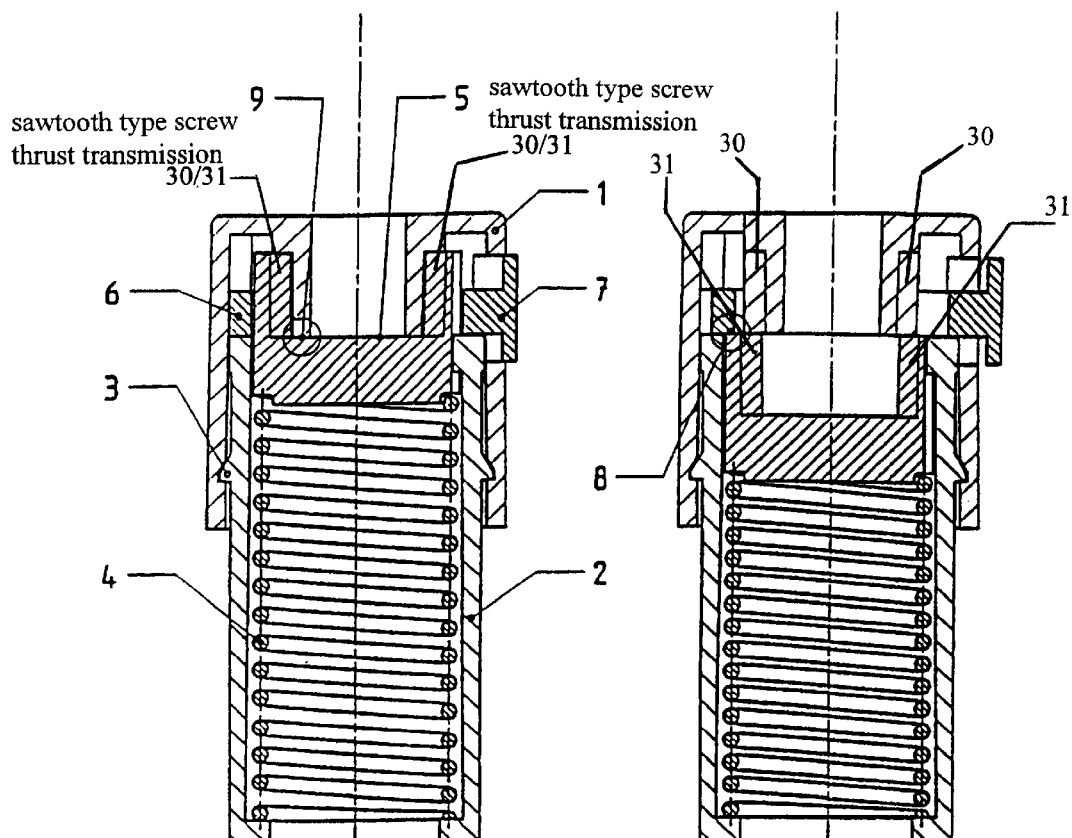
FIG. 1a is a view in longitudinal section through a locking-stressing-mechanism according to the invention wit the locking member disengaged and the spring in its released position.
FIG. 1b is a similar view of the same mechanism with the locking member engaged and the spring in its compressed position.

FIG. 1a is a view in vertical longitudinal section through a locking-stressing-mechanism. The upper cylindrical housing portion 1 engages over the spring housing 2 to which it is connected by way of snap engagement projections 3. The snap-engagement projections 3 are disposed on he outside of the spring housing 2 and extend over two mutually oppositely disposed circular segments each of about 30°. They engage into a peripherally extending groove on t inside of the upper housing portion. The two housing portions are therefore rotatable relative to each other. Disposed in the spring housing 2 is a compression spring 4 Which is generally already prestressed when the two housing portions are fitted together. The compression spring 4 is supported on a peripherally extending projection at the lower end of the spring housing and on the output drive member 5 which is arranged displaceably in axis-parallel relationship between the upper housing portion and the spring housing and which in turn presses against the upper housing portion 1. The cyindrical cup-shaped output drive member is mounted slidably in the cylindrical bore of housing 2 but projects into the upper housing portion. The annular locking member 6 e (tends around the output drive member. The release button 7 which is mounted on the locking member projects laterally out the upper housing portion. In the preferred arrangement the member 5 is a flange on a hollow piston (not shown) reciprocable in a cylinder (not shown) in the upper housing portion which is connected to a reservoir (not shown), the whole mechanism being part of an atomiser.

In the case of a screw-type thrust transmission means the collar of the cup-shaped output drive member generally includes two sawtooth-shaped recesses against which two saw teeth in the upper housing portion slid . The saw teeth and recesses are shown in highly simplified form in FIG. 1a and 1b at 30, 31. When the upper housing portion is rotated relative to the spring housing the output drive member is urged further into the spring housing against the force of the compression spring. As soon as the upper edge of the output drive member has been urged downwardly sufficiently far through the locking member, the annular locking member is displaced perpendicular to the axis of the housing between the upper edge of the output drive member and an annular projection in the upper housing portion and holds the out drive member and the compression spring which is (additionally) stressed by the displacement of the output drive member, fast in the position attained.

The average spring force is 10 to 150 N. Between the upper and lower rest position of the output drive member the spring force alters approximately by ±10% of the average spring force.

Pressing the release button 7 causes the annular locking member to be pushed back perpendicularly to the axis of the housing whereby the path of movement of the output drive member is c eared. The compression spring pushes the output drive member upwardly over a predetermined distance and in so doing actuates a component (not shown) which is connected to the output drive member, for example a piston in a cylinder.

FIG. 1a shows the locking-stressing-mechanism with the output drive member in its upper rest position and with the locking member disengaged. FIG. 1b shows the locking-stressing-mechanism with a member in its lower rest position and with the locking member engaged. The abutment 8 is the means for delimiting the travel of the output drive member in the lower rest position thereof while the abutment 9 is the means for delimiting the travel in the rest position thereof. Rotation of the two housing portions relative to each other causes the mechanism to go from the condition shown in FIG. 1a into the condition shown FIG. 11b. Pressing the release button causes the mechanism to go from the condition shown in FIG. 11b into the condition shown in FIG. 1a.

Figures 2A, 2B:
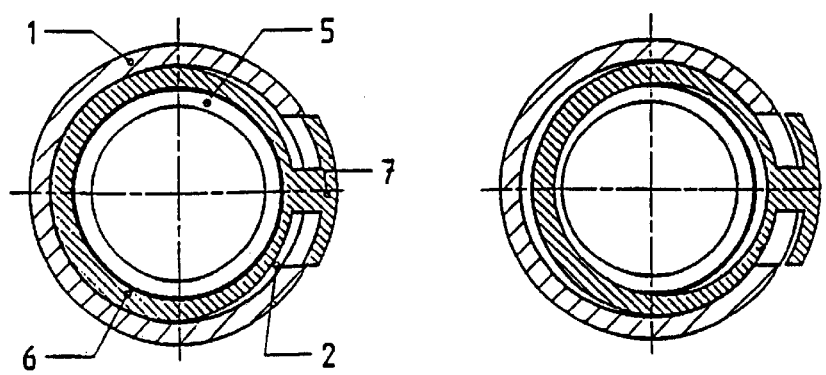
FIGS. 2a and 2b are horizontal section views corresponding to FIGS. 1a and 1b and showing the locking member in its disengaged and engaged positions respectively.

FIGS. 2a and 2b show a view cross-section through the locking-stressing-mechanism at the level of the middle of the annular locking member, more specifically FIG. 2a corresponding to the condition of the locking-stressing-mechanism as shown in FIG. 1a in the disengaged position of the locking member and FIG. 2b corresponding to the condition of the locking-stressing-mechanism as shown in FIG. 1b with the locking member in the engaged position.

FIGS. 3a to 6b show a number of embodiments according to the invention a f the annular locking member, more specifically partly in Cross-section approximately at the level of the middle of the annular locking member and partly as a plan view with the bottom of the upper housing portion in section. FIGS. 3a, 4a, 5a and 6a show the locking member in the disengaged position while FIGS. 3b, 4b, 5b and 6b show the looking member in the engaged position.

Figure 3A:
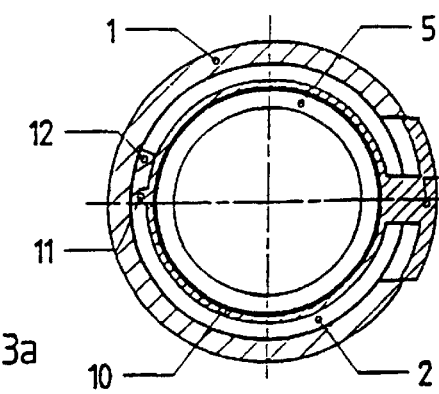
FIGS. 3a and 3b are views similar to FIGS. 2a and 2b showing a second embodiment of the locking member.
Figure 3B:
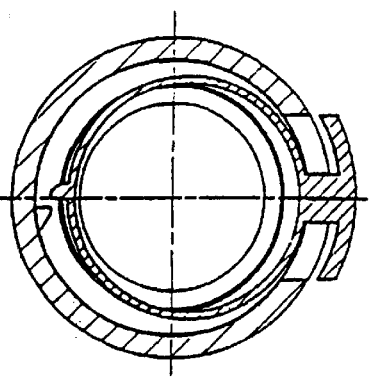

In FIGS. 3a and 3b a bevelled cam projection 11 is disposed on the outer peripheral surface of the locking member 10. A further bevelled cam projection 12 is disposed on the upper edge of the spring housing 2. Towards the end of the rosary movement of the upper housing portion relative to the spring housing the two cam projections come to bear against each other with their bevelled sides and the car projection on the spring housing pushes the locking member 10 into the engaged position. When the release button is actuated the locking member is pushed back into the disengaged position and the path of movement of the output drive member is cleared.

Figure 4A:
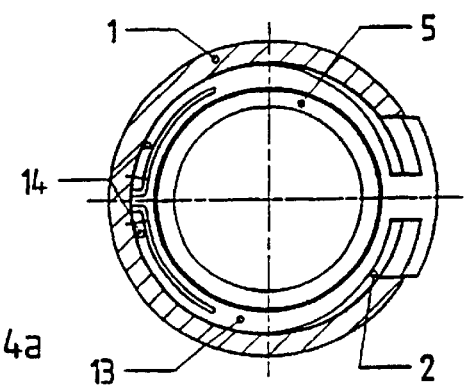
FIGS. 4a and 4b are views similar to FIGS. 2a and 2b showing a third embodiment of the locking member.
Figure 4B:
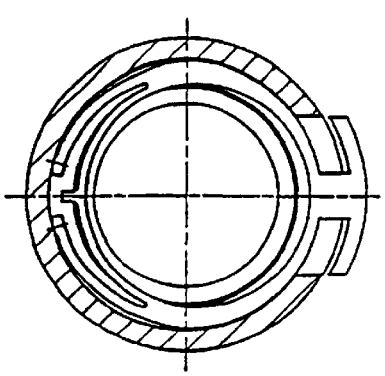

In FIG. 4a the locking member 13 is provided with two integrated springs 14 which urge the locking member in the upper rest position of the locking-stressing-mechanism against the outer peripheral surface of the output drive member 5. As soon as the upper edge of the output drive member 5 has been pressed through the locking member the locking member is displaced by the force of the integrated springs into the engaged position shown in FIG. 4b. When the release button is actuated the locking member is pushed back into the disengaged position against the force of the integrated springs and the path of movement of the output drive member is cleared.

Figure 5A:
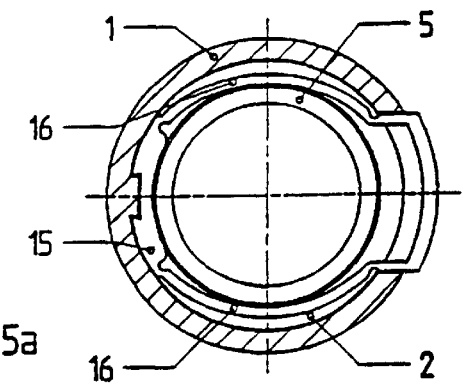
FIGS. 5a and 5b are views similar to FIGS. 2a and 2b showing a fourth embodiment of the locking member.
Figure 5B:
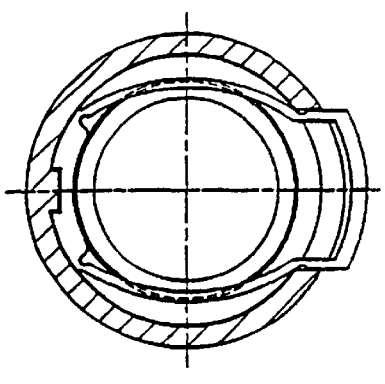

FIG. 5a shows a locking member 15 whose prestressed arcuate portions 16 initially press against the outer peripheral surface of the output drive member 5. As soon as the upper edge of the output drive member has been pressed through the locking member the prestressed arcuate portions 16 jump over the upper edge of the output drive member into the engaged position. When the release button is actuated the arcuate portions 16, by virtue of their bending loading, are urged outwardly and clear the way for displacement of the output drive member.

Figure 6A:
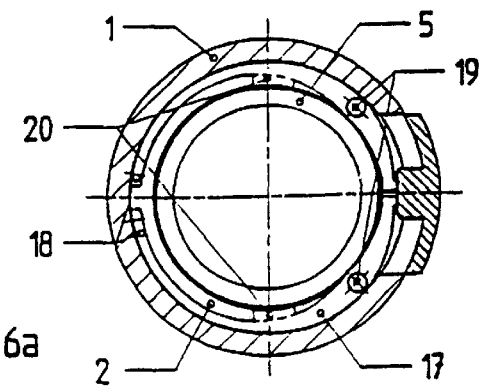
FIGS. 6a and 6b are views similar to FIGS. 2a and 2b showing a fifth embodiment of the locking member.
Figure 6B:
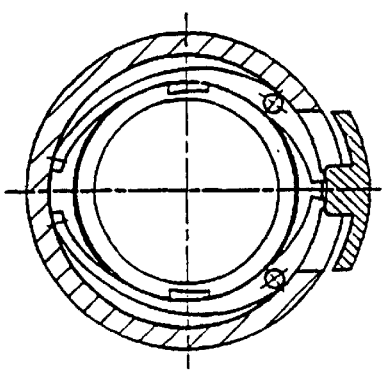

FIG. 6a shows a two-part locking member 17 with integrated springs. Each spring portion 18 is rotatably mounted on an axis 19. A projection 20 is disposed on the inside of each spring portion. As soon as the upper edge of the output drive member has been pressed through the locking member the projections 20 jump over the upper edge of the output drive member into the engaged position. When the release button is actuated the spring portions 18 are urged outwardly with the projections 20 and clear the way for displacement of the output drive member. A A locking-stressing-mechanism as just described with reference to the drawings has the following advantages:

- It is simple and reliable to operate even by unskilled persons.
- It can be triggered with one hand by pressing the release button.
- When using a force step-up transmission means, for example a screw thrust transmission mean', it is possible to produce a high spring force by means of a low level torque.
- The movement of the locking member can be positively coupled to the rotary movement for stressing the spring in a simple manner.
- It can be produced economically and is easy to assemble.
- It comprises functional elements which have a low rate of wear and it is reliable in operation.
- It is compact and can easily be adapted to a miniaturised high-pressure atomizer. The metering effect is very accurate because of the defined abutments for the output drive member.

What is claimed is:

1. A locking-stressing-mechanism for a spring-actuated output drive device, the mechanism comprising:
   an upper housing portion;
   a spring housing;
   a cup-shaped output drive member;
   a spring acting on said output drive member to cause said output drive member to act as a quick-motion member, said output drive member being arranged to move a piston in a cylinder to compress fluid therein;
   a locking member;
   a first abutment touching said output drive member in its upper rest position;
   a second abutment touching said output drive member in its lower rest position, both of said first and second abutments serving for delimiting the travel of said output drive member;
   means for releasing the displaceably arranged locking member; and
   force step-up transmission means for stressing said spring, wherein said force step-up transmission means comprises a screw thrust transmission means including at least one sawtooth-shaped recess in a collar of said cup-shaped output drive member against which at least one sawtooth in sad upper housing portion slides,
   wherein said upper housing portion and said spring housing are connected with each other by way of snap-engagement projections and are rotatable relative to each other and, by rotating urge said output drive member into said spring housing against the force of said spring, and
   wherein positively couple to the movement of said output drive member is the movement of said locking member which snaps into alignment with a top portion of the collar of said output drive member to form said second abutment when said output drive member reaches its lower rest position holds said output drive member and said compression spring in the stressed position, and
   wherein said locking member is displaceable in a plane substantially perpendicular to the longitudinal axis of locking-stressing-mechanism, and
   wherein said means for displacing the locking member is a release button which is combined with or attached to said locking member and is operated in the lower rest position of said output drive member by pressing, whereby said locking member is moved out of the path of said output drive member, thereby releasing said output drive member from the lock position so that said compression spring pushes said output drive member to the upper rest position.

2. A mechanism according to claim 1, wherein the locking member comprises an open or closed ring which is arranged displaceably in a plane perpendicular to the axis of the locking-stressing-mechanism.

3. A mechanism according to claim 1, wherein said locking member comprises a radially deformable elastic ring, or a rigid ring with leaf springs formed thereon, or a rigid ring with a cam projection, or a rigid ring and a metal spring.

4. A mechanism according to claim 1, wherein said locking member is made of plastics or metal.

5. A device for c and atomizing fluid comprising a mechanism according to claim 1.

6. A device according to claim 5, which comprises a metered dose atomiser.

7. A device according to claim 5, which comprises a miniaturized high-pressure metered dose atomiser.

* * * * *

UNITED STATES PATENT AND TRADEMARK OFFICE
CERTIFICATE OF CORRECTION

PATENT NO. : 6,453,795 B1
DATED : September 24, 2002
INVENTOR(S) : Eicher et al.

It is certified that error appears in the above-identified patent and that said Letters Patent is hereby corrected as shown below:

Title page,
Item [54], Title, delete "LOCKING MECHANISM FOR A SPRING-ACTUATED DEVICE" and replace with -- LOCKING-STRESSING-MECHANISM FOR A SPRING-ACTUATED DEVICE --.

Column 1,
Line 32, delete "provide d" and replace with -- provided --.
Line 35, delete "incorported" and replace with -- incorporated --.

Column 2,
Line 29, delete "0o" and replace with -- into --.

Column 3,
Line 21, delete "wit" and replace with -- with --.
Line 41, delete "snap engagement" and replace with -- snap-engagement --.
Line 42, delete "he" and replace with -- the --.
Line 45, delete "on t" and replace with -- on the --.
Line 48, delete "Which" and replace with -- which --.
Lines 58 and 59, delete "e(tends" and replace with -- extends --.

Column 4,
Line 2, delete "slid" and replace with -- slide --.
Line 12, delete "out" and replace with -- output --.
Line 23, delete "c earned" and replace with -- cleared --.
Line 31, delete "a" and replace with -- the output drive --.
Lines 39 and 40, delete "11b" and replace with -- 1b --.
Line 51, delete "a f" and replace with -- of --.
Line 52, delete "Cross-section" and replace with -- cross-section --.
Line 62, delete "rosary" and replace with -- rotary --.
Line 64, delete "car" and replace with -- cam --.

Column 5,
Line 34, delete "A" after "member."
Line 42, delete "mean" and replace with -- means --.

UNITED STATES PATENT AND TRADEMARK OFFICE
CERTIFICATE OF CORRECTION

PATENT NO. : 6,453,795 B1
DATED : September 24, 2002
INVENTOR(S) : Eicher et al.

It is certified that error appears in the above-identified patent and that said Letters Patent is hereby corrected as shown below:

<u>Column 6,</u>
Line 26, delete "couple" and replace with -- coupled --.
Line 36, delete "of locking-stressing-mechanism" and replace with -- of the locking-stressing-mechanism --.
Line 57, delete "for c" and replace with -- for compressing --.

Signed and Sealed this

Eighth Day of June, 2004

JON W. DUDAS
*Acting Director of the United States Patent and Trademark Office*